United States Patent [19]

Hutchison et al.

[11] 4,069,236

[45] Jan. 17, 1978

[54] ALUMINUM ACYLOXIDES

[75] Inventors: Robert B. Hutchison, Cincinnati, Ohio; C. William Blewett, Fort Mitchell, Ky.

[73] Assignee: Emery Industries, Inc., Cincinnati, Ohio

[21] Appl. No.: 185,805

[22] Filed: Oct. 1, 1971

[51] Int. Cl.$^2$ .............................................. C11C 1/00
[52] U.S. Cl. .................................. 260/414; 260/2M; 260/409
[58] Field of Search ........................... 260/414, 2 M

[56] References Cited

U.S. PATENT DOCUMENTS

| 2,741,629 | 4/1956 | Cohen | 260/414 X |
| 2,751,361 | 6/1956 | Van Strien et al. | 260/414 X |
| 2,801,190 | 7/1957 | Orthner et al. | 260/414 X |
| 2,892,780 | 6/1959 | Rinse | 260/414 X |
| 2,925,430 | 2/1960 | Stedehouder et al. | 260/414 |
| 3,355,402 | 11/1967 | Sasaki et al. | 260/414 X |

FOREIGN PATENT DOCUMENTS 250,809  10/1960  Australia .............................. 260/2 M

*Primary Examiner*—Ethel G. Love
*Attorney, Agent, or Firm*—John D. Rice

[57] ABSTRACT

Aluminum acyloxide polymers are formed in a reaction involving approximately equimolar amounts of aluminum alkoxide, water and a branched chain, saturated aliphatic monocarboxylic acid having from about 10 to about 25 carbon atoms. These novel compounds from stable gels with non-polar liquids.

4 Claims, No Drawings

ALUMINUM ACYLOXIDES

BACKGROUND OF THE INVENTION

Aluminum acyloxide polymers can be formed by the reaction of aluminum alkoxides and fatty acids. For example, U.S. Pat. No. 2,744,074 to Theobald discloses a process for reacting aluminum alkoxide and fatty acid to obtain compounds which correspond structurally to the formula

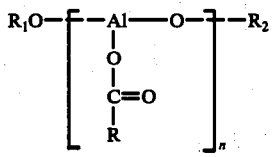

Wherein R is an alkyl group and $n$ is a whole number of at least 16. In addition, U.S. Pat. No. 2,979,497 to Rinse discloses a process for forming cyclic aluminum acyloxides by reacting approximately equimolar amounts of aluminum alkoxide, water and fatty acid. The compounds formed are disclosed to be useful as gelling agents and thickening agents for alkyd resins, drying oils, glyceride oils, mineral oils, paraffins and other hydrocarbons.

While aluminum acyloxide polymers disclosed in the prior art can be useful gelling agents for mineral oils, paraffins and other hydrocarbons, the gels formed are not completely satisfactory in that the gels are stable for only a short period of time before syneresis occurs. In addition, the gels formed commonly exhibit a colored and/or cloudy appearance. In many commercial applications it is desirable to form gels which are stable and exhibit an appearance which is clear and colorless.

SUMMARY OF THE INVENTION

This invention involves novel aluminum acyloxide polymer compounds, a process for forming the compounds, and compositions in which they are an essential ingredient.

The novel aluminum acyloxides of this invention correspond structurally to the formula

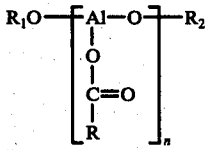

Wherein R is a branched chain, saturated, aliphatic radical containing from about 9 to 24 carbon atoms, $R_1$ and $R_2$ are either the same or different lower alkyl groups or acyl groups having 9 to 24 carbon atoms, and $n$ is a whole number.

The novel process for forming the aluminum acyloxide compounds of this invention involves reacting approximately equimolar amounts of aluminum alkoxide, water and a branched chain, saturated aliphatic monocarboxylic acid containing from about 10 to about 25 carbon atoms.

The invention also encompasses unusually stable gels prepared from the aluminum acyloxides of the invention and certain non-polar liquids.

DISCUSSION OF THE INVENTION AND ITS PREFERRED EMBODIMENTS

As noted above, this invention relates to novel aluminum acyloxide polymers which form unexpectedly stable gels with certain non-polar liquids. The gels are useful in cosmetic preparations, for example, as bases in cosmetic formulations such as facial creams and hand creams. In a preferred embodiment of this invention, the aluminum acyloxides are formed by a process such that they impart substantially no color or opacity to the non-polar liquid gels.

The novel aluminum acyloxides of this invention have the structural formula

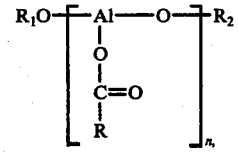

Wherein R is a branched chain saturated aliphatic hydrocarbon group containing from about 9 to about 24 carbon atoms, $R_1$ and $R_2$ are either the same or different lower alkyl groups or acyl groups having 9 to 24 carbon atoms, and $n$ is a whole number of from about 5 to about 60.

Preferably R is a branched chain saturated aliphatic hydrocarbon group containing from about 1 to 3 alkyl groups, and $R_1$ and $R_2$ are either alkyl groups having 2 to 3 carbon atoms, or acyl groups having about 18 carbon atoms and $n$ is a whole number of from about 10 to about 25.

The alkyl groups attached to the branched chain acids from which the materials of this invention are derived are lower alkyl groups preferably containing from about 1 to 2 carbon atoms. It has been found that the effectiveness of the aluminum acyloxides of this invention in forming stable gels is enhanced when the branching occurs toward the middle of the acid molecule. The alkyl branch of the branched chain acids of the invention should preferably occur at least two carbon atoms from the carboxyl group (in the $\beta$ position or higher) and at least two carbon atoms from the opposite end carbon in the chain. For example, if the branched acid is methyl heptadecanoic acid (isostearic acid) the methyl groups should not be attached to the No. 1 2, 16 or 17 carbon atoms (obviously no branching could occur at the No. 1 position).

It is a notable aspect of this invention that the monocarboxylic acid used to form the aluminum acyloxides of this invention must be a branched chain, saturated, aliphatic monocarboxylic acid containing from about 16 to about 25, preferably about 18, carbon atoms.

The branched chain, saturated, aliphatic group R referred to in the structural formula set forth above is in effect the hydrocarbyl or non-carboxyl portion of normally liquid, branched chain, saturated, aliphatic monocarboxylic acids containing from about 16 to 25 carbon atoms. The branched chain monocarboxylic acids employed in the formation of the aluminum acyloxides of this invention are liquid at room temperature and are usually prepared by synthetic methods. An acid particularly suited for use in the preparation of the aluminum acyloxides which form the basis of this invention is one containing 18 carbon atoms formed as a by-product in the polymerization of naturally occurring unsaturated fatty acids in accordance with the method described in U.S. Pat. No. 2,812,342 (hereinafter referred to as the U.S. Pat. No. 2,812,342 and identified as isostearic acid). The U.S. Pat. No. 2,812,342 disclosure is incorporated herein by reference. According to the disclosure of the U.S. Pat. No. 2,812,342, monounsaturated or polyunsaturated fatty acids are treated thermally in the presence of water with or without a catalyst to produce products which are known commercially as dimer acids. This process inherently produces a substantial amount of by-product acids which are a mixture of monomeric acids. The monomer mixture, which is normally distilled in vacuo from the polymer-containing reaction product, includes saturated fatty acids which have not been affected by the polymerization treatment, probably some unsaturated fatty acids which have not been affected by the polymerization treatment and some which have been modified in such a way that they resist further polymerization.

Following the procedure outlined in the U.S. Pat. No. 2,812,342, the monomeric fatty acids are hydrogenated to reduce the iodine value of the mixture to a level below 10 and perhaps as low as 3, thereby reducing any natural unsaturated fatty acids which may be present to saturated fatty acids. The hydrogenation treatment also reduces the iodine value of the fatty acids which have been structurally modified in some degree by the polymerization treatment. Further modifications may take place during the hydrogenation although it is not known to what extent structural modification of the acids takes place during that step. The resulting hydrogenated fatty acid mixture is then solvent separated to remove the normal solid fatty acids, such as stearic and palmitic acids. The remaining saturated fatty acid is a modified product which, while containing 18 carbon atoms, possesses a branched chain structure, a titer below 15° C., an iodine value of substantially 3 to 10 and is referred to as isostearic acid. The exact structure of isostearic acid is not know; however, nuclear magnetic resonance tests have indicated that it is branched and has predominantly one alkyl group, a methyl group, per molecule.

The isostearic acid described above and in the U.S. Pat. No. 2,812,342 forms, when converted into an aluminum acyloxide of this invention, a preferred embodiment of this invention, designated herein as aluminum isostearyloxide.

The novel process involved in forming the aluminum acyloxides of this invention comprises reacting aluminum alkoxide having the formula Al (OR')$_3$ wherein R' is an alkyl radical, preferably a lower alkyl radical, and more preferably one having about 2 to 3 carbon atoms, water and branched chain, saturated, aliphatic monocarboxylic acid containing from about 16 to about 25 carbon atoms. The molar ratio of the alkoxide, water, and branched chain monocarboxylic acid can vary to some extent but is preferably about 1:1:1 respectively. The reaction is conducted at a temperature of from about 50° to about 100° C., until the liberation of alcohol ceases. Preferably, the alcohol liberated is removed by distillation as the reaction proceeds.

While the mechanism of the reaction is not definitely known, apparently a condensation polymerization occurs with the liberation of alcohol. This reaction can be represented as follows

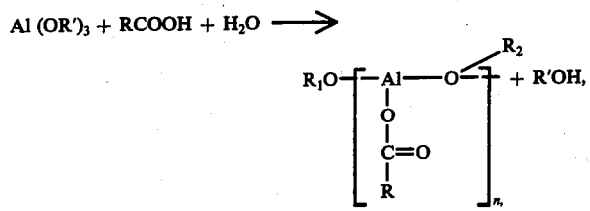

wherein $R_1$ and $R_2$ are either lower alkyl groups (R') or acyl groups (RCO—), R is a branched-chain, saturated, aliphatic hydrocarbon group, and $n$ is a whole number preferably of from about 5 to 60 and more preferably about 10 to 25.

While many aluminum alkoxides can be utilized in the practice of this invention, it is preferred that the aluminum alkoxide is derived from lower molecular weight alcohols so that the alcohol liberated in the process of the reaction can be easily removed by distillation. It is preferred that the aluminum alkoxide be derived from alcohols having from about 2 to 5 carbon atoms, as for example, ethanol, normal and isopropanol, butanol and pentanol. The preferred aluminum alkoxide is aluminum isopropoxide.

The aluminum acyloxides of this invention form unsually stable gels with cetain non-polar liquids. Also they impart little or no color and/or opacity to non-polar liquids and enable the preparation of colorless or clear gels when made with colorless or clear non-polar liquids.

In a specific and preferred embodiment of the process of this invention, aluminum isopropoxide is dissolved in a suitable inert solvent such as toluene. Other examples of suitable inert solvents are benzene, petroleum ether and tetrahydrofuran. To the resulting solution which is maintained at a temperature of about 85° C., is added solution comprising branched-chain saturated monocarboxylic acid, water and alcohol. The alcohol, preferably isopropanol, is added to aid the formation of a solution of the monocarboxylic acid and water.

After the addition of the solution of monocarboxylic acid, water and alcohol to the solution of aluminum alkoxide is completed, the mixture is distilled to remove the added alcohol and alcohol formed in the reaction. When isopropanol is to be removed, the distillation is preferably accomplished at atmospheric pressure and at a temperature of from 85° to about 110° C.

Removal of the alcohol leaves a solution of the aluminum acyloxide product in inert solvent, e.g. toluene.

The aluminum acyloxide is in its free state a solid and is obtained by evaporating the inert solvent such as toluene from the solution. The evaporation can be effectively conducted at atmospheric or reduced pressure at a temperature which does not affect the aluminum acyloxide product. Temperatures of from about 40° to about 110° C. are suitable.

An alternative method for preparing the aluminum acyloxides of this invention is to react the aluminum alkoxide, water and branched chain acid in the presence of a non-polar liquid with which it is desired to form a gel. The non-polar liquids described herein are suitable for such a purpose. After the reaction in the presence of a non-polar liquid is completed, the amount of liquid can be adjusted to provide the ratio thereof to aluminum acyloxide which will produce optimum gel properties. Usually additional non-polar liquid must be added to the resulting reaction mixture to obtain the optimum ratio because it is not economical to conduct the reaction with the amount of liquid required to obtain optimum gel forming properties.

By preparing the aluminum acyloxides in the presence of a non-polar liquid solvent with which it is desired ultimately to form a gel, certain advantages are derived. For example using this method enables one to avoid the difficulties of working with a gelatinous product which sometimes results when the last traces of solvent are removed from the aluminum acyloxide when it is prepared as a powder, and this method permits formation of a gel without the need for dissolving dry aluminum acyloxide, which requires the use of relatively high temperatures.

In a preferred embodiment of the process of this invention the aluminum acyloxide formed is passed, while still in solution in the inert solvent, through a filter capable of retaining particles 1 micron and larger. Suitable filters include filter paper, fine mesh nylon silk screens, and the like. Prior to filtering the solution of aluminum acyloxide and inert solvent, it is often desirable to add to the solution a filter aid, as for example diatomaceous earth, dicalite or other finely divided inert solids. The filtrate is then evaporated as described above. This preferred process provides aluminum acyloxide gelling agents which impart little or no opacity to the non-polar liquids and the resulting gels formed.

If the aluminum acyloxide is to be used as a gelling agent, it is preferred that it be ground to a powder which will pass a 25 mesh U.S. standard screen.

As noted previously, stable gel compositions comprising aluminum acyloxide polymers of this invention and certain non-polar liquids can be formed. The non-polar liquids useful in forming gel compositions of this invention are non-polar compounds which are liquid at 25° C. and have a dielectric constant of less than 6. Among the suitable non-polar liquids are hydrocarbons, chlorinated hydrocarbons and esters which are liquid at 25° C. and have a dielectric constant of less than 6. Especially suitable non-polar liquids are saturated and unsaturated aliphatic and aromatic hydrocarbons having from about 5 to about 50 carbon atoms.

Examples of suitable non-polar liquids are isopropyl myristate, isopropyl stearate, isopropyl palmitate, isopropyl oleate, chloroform, carbon tetrachloride, methylene chloride, 1,1,1-trichloroethane, ethylene dichloride, propylene dichloride, trichlorethylene, perchloroethylene, monochlorobenzene, orthodichlorobenzene, trichlorobenzene and hydrocarbons such as pentane, hexane, heptane, octane, nonane, decane, undecane, dodecane, tridecane, tetradecane, pentadecane, hexadecane, heptadecane, benzene, toluene and xylene. Especially preferred hydrocarbons are complex mixtures of liquid hydrocarbons such as petroleum ether, mineral spirits, mineral oil, naptha and turpentine.

The novel gel compositions of this invention comprise from about 3 parts to about 30 parts by weight of the aluminum acyloxides of this invention and from about 70 parts to about 97 parts by weight of non-polar liquid. Preferably the gels comprise from about 3 parts to about 15 parts by weight of the aluminum acyloxides and from about 85 parts to about 97 parts by weight of the non-polar liquid.

The process for forming the gels comprises dissolving from about 3 parts to about 30 parts by weight, preferably 3 parts to 15 parts by weight, of aluminum acyloxide of this invention in from about 70 parts to about 97 parts by weight, preferably 85 parts to 97 parts by weight, of a non-polar liquid. In order to aid dissolution of the aluminum acyloxide in the non-polar liquid it is preferred that the aluminum acyloxide be in a particulate form comprising particles which will pass a 25 mesh U.S. standard screen. Dissolving the aluminum acyloxide in the non-polar liquid is often aided by stirring and heating the mixture of aluminum acyloxide and non-polar liquid. For example, the mixture can be heated to a temperature of from about 50° to about 200° C., preferably from about 50° to about 130° C.

Gel formation may be enhanced by adding to the aluminum acyloxide — non-polar solvent solution a carboxylic acid. Many carboxylic acids may be used for this purpose, including aliphatic and aromatic acids having from about 6 to about 54 carbon atoms, preferably about 6 to 36 carbon atoms, specific examples of which are benzoic acid, hexanoic acid, stearic acid, dimer acid, (polymerized unsaturated $C_9 - C_{22}$ fatty acid) preferably polymerized tall oil fatty acids or oleic, and branched aliphatic acids such as isostearic acid. The amount of carboxylic acids which may be used varies with the non-polar liquid used and the specific properties of the gel which are sought but generally best results are achieved when from 25 to 75 parts are used per 100 parts of aluminum acyloxide.

The gels formed in the process of the invention can be thickened pourable liquids or solids at 25° C. depending on the particular non-polar liquid components and the amount of the aluminum acyloxide and carboxylic acid added to the non-polar liquid.

The following examples are presented to particularly illustrate the invention disclosed herein, the examples are not intended to be limitations on the invention.

EXAMPLE I

Several aluminum acyloxides were prepared in the following manner:

a. Two hundred and four grams (1 mole) of aluminum isopropoxide were dissolved in 300 ml. of toluene in a flask equipped with a stirrer, addition funnel and distilling head. To this solution maintained at a temperature of 80° C., there was added with rapid stirring a solution consisting of 18.0 grams (1 mole) of water, 200 ml. of isopropanol and 284 grams (1 mole) of isostearic acid sold under the trademark EMERY 875. After the addition was complete, the resulting mixture was distilled at atmospheric pressure until the refractive index of the distillate indicated that it was pure toluene. The mixture was then placed on a steam bath and the remaining toluene was evaporated. The white solid recovered was an aluminum isostearyloxide polymer having a molecular weight of about 4000. The molecular weight of this and other polymers described herein was determined by vapor pressure osometry.

b. The procedure of paragraph (a) above was followed except that when the refractive index of the distillate indicated that it was pure toluene, the mixture was allowed to cool to room temperature (25° C). A small amount (30 grams) of a filter aid, dicalite was added to the mixture and the mixture was filtered through medium fast filter paper that retains particles 1 micron and larger. The filtrate was then evaporated on a steam bath as in Paragraph (a) above. The white solid recovered was an aluminum isostearyloxide polymer having a molecular weight of 4000, and will hereinafter be designated as filtered aluminum isostearyloxide.

c. The same procedure as described in Paragraph (a) above was followed except that 284 grams (1 mole) of stearic acid was used in place of isostearic acid and aluminum stearyloxide polymer was obtained. It had a molecular weight of 9500.

d. The same procedure as described in Paragraph (a) above was followed except 228 grams (1 mole) of myristic acid was used in place of isostearic acid and aluminum myristyloxide polymer was obtained.

Each of the aluminum acyloxides formed above is a gelling agent. Paragraphs (a) and (b) are examples of particular embodiments of the invention disclosed herein; Paragraphs (c) and (d) do not represent examples of the invention and are provided for comparison to illustrate advantages of the invention.

EXAMPLE II

Mineral oil gels were formed in this example. Each of the aluminum acyloxide products prepared in Example I above was separately ground in a mortar and pestle to a powder fine enough to pass a 25 mesh U.S. standard screen. The mineral oil employed had a boiling range of from 240° to 350° C. and a Brookfield viscosity (1 rpm) at 25° C. of 70 cps. Four samples of this mineral oil weighing 910 grams each were placed in separate flasks equipped with a stirrer and heated to a temperature of 150° C. To each of these samples was added 30 grams of isostearic acid and 60 grams of one of the aluminum acyloxide gelling agents found in Example I. The resulting mixtures were stirred vigorously. When the aluminum acyloxide had dissolved, the mixture was cooled to room temperature (25° C.). The resulting gels were designated A, B, C and D and had the following characteristics:

| GELS | ALUMINUM ACYLOXIDE (Gelling Agent) | VISCOSITY Brookfied 1 rpm 25° C. | COLOR | CLARITY | STABILITY |
| --- | --- | --- | --- | --- | --- |
| A | Aluminum isostearyloxide | 3,000,000 cps | colorless | cloudy | no syneresis one month after preparation |
| B | Filtered Aluminum Isostearyloxide | 3,000,000 cps | colorless | clear | no syneresis one month after preparation |
| C | Aluminum stearyloxide | non-pourable gel; viscosity not determined | colorless | cloudy | syneresis observed two hours after preparation |
| D | Aluminum myristyloxide | non-pourable gel viscosity not determined | colorless | cloudy | syneresis observed two hours after preparation |

As may be seen from the data, Gels A and B, embodiments of this invention, have markedly greater stability than the comparative gels C and D which show syneresis, i.e., separation of oil from the gel, occurring shortly after preparation.

EXAMPLE III

A mineral oil is formed in the following manner: nine hundred and fifty grams of the mineral oil employed in Example II are heated to a temperature of 150° C. To this heated mineral oil is added during rapid stirring a mixture comprising 20 grams of polymerized unsaturated fatty acid sold under the trademark EMPOL 1010 and 30 grams of filtered aluminum isostearyloxide. When the mixture has dissolved, the stirring is ceased and the resulting mineral oil solution is cooled to room temperature (25° C.).

The resulting mineral oil gel has a Brookfield viscosity of 1,500,000 cps (2.5 rpm) (25° C.). The gel is clear and colorless. No syneresis occurs within one month after preparation of this gel.

EXAMPLE IV

A mineral spirit gel is formed using a mineral spirit having boiling range of 118° to 143° C. and a Brookfield viscosity of 1 cps (1 rpm) (25° C.). Nine hundred and thirty grams of this mineral spirit, 10 grams of the dimer acid described in Example III above and 60 grams of filtered aluminum isostearyloxide are placed in a flask equipped with a stirrer and reflux condenser. The mixture is heated so that it gently refluxes and is stirred until the aluminum isostearyloxide and dimer acid are dissolved. The solution is allowed to cool to room temperature (25° C.).

The resulting mineral spirit gel formed has a Brookfield viscosity of 700,000 cps (1 rpm) (25° C.). The gel is clear and colorless and shows no syneresis after one month.

EXAMPLE V

A chloroform gel is formed in the following manner: nine hundred and thirty grams of chloroform, 10 grams of isostearic acid, and 60 grams of filtered aluminum isostearyloxide are placed in a flask equipped with a stirrer and reflux condenser. The mixture is heated so that it gently refluxes and is stirred until the aluminum isostearyloxide and isostearic acid are dissolved. The solution is allowed to cool to room temperature (25° C.). The resulting gel is clear and colorless.

EXAMPLE VI

An isopropyl myristate gel is formed in the following manner: nine hundred and fifty grams of isopropyl myristate and 50 grams of aluminum isostearyloxide are placed in a flask equipped with a stirrer. The mixture is heated to a temperature of 150° C. and is stirred until the aluminum isostearyloxide is dissolved. Then the solution is cooled to 25° C. The gel has good color, but is less stable than the hydrocarbon gels. However, it is substantially more stable than a gel prepared from the aluminum acyloxide of Example II (c).

EXAMPLE VII

A mixture of 700 grams of a mineral oil having a viscosity of 70 cps and 204 grams (1 mol) of aluminum isopropoxide were heated to 130° C. under a nitrogen blanket, maintained at that temperature while the solution of 284 grams (1 mol) of isostearic acid sold under the trademark EMERY 875 and 18 grams (1 mol) of water in 150 ml. of isopropanol were added over a period of one half hour. During the addition, isopropanol that distilled off was collected. After the addition was completed the solution was maintained at 130° C. until no further isopropanol distilled off. The solution was then filtered with the aid of Dicalite after it had cooled to room temperature. A gel was made from the resulting filtered aluminum acyloxide solution by heating 34.7 grams of the solution, 57.3 grams of mineral oil (70 viscosity) and 8 grams of isostearic acid to 150° C. and allowing the solution formed to cool. This gel had essentially the same properties as the one described in Example II (a) above.

A gel may be formed in the same manner as is described above by allowing the solution prepared as above to stand for about a week rather than by heating.

What is claimed is:

1. Aluminum acyloxides having the formula

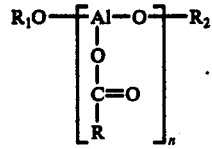

wherein R is a branched chain, saturated, aliphatic radical containing from about 9 to about 24 carbon atoms, $R_1$ and $R_2$ are either lower alkyl groups or acyl groups, and $n$ is a whole number of between 5 and 60.

2. The aluminum acyloxides of claim 1 wherein said branched chain radical has a lower alkyl group spaced at least two carbon atoms from the carbonyl group and two carbon atoms from the terminal carbon atom of said radical.

3. The aluminum acyloxide of claim 2 wherein said lower alkyl group of said branched chain radical is a lower alkyl group having 1 to 3 carbon atoms.

4. The aluminum acyloxide of claim 2 wherein R is the hydrocarbon radical of isostearic acid.

* * * * *